(12) United States Patent
Netzer (10) Patent No.: US 6,373,263 B1
(45) Date of Patent: Apr. 16, 2002

(54) DIFFERENTIAL WINDSHIELD CAPACITIVE RAIN SENSOR

(75) Inventor: Yishay Netzer, Yuvalim (IL)

(73) Assignee: Millennium Sensors Ltd., Yuvalim (IL)

( * ) Notice: Subject to any disclaimer, the term of this patent is extended or adjusted under 35 U.S.C. 154(b) by 0 days.

(21) Appl. No.: 09/553,900

(22) Filed: Apr. 20, 2000

(51) Int. Cl.[7] .............................................. G01R 27/26
(52) U.S. Cl. ...................................... 324/665; 324/669
(58) Field of Search ................................ 324/665, 658, 324/663, 664, 669, 679

(56) References Cited

U.S. PATENT DOCUMENTS

| | | | |
|---|---|---|---|
| 4,016,490 A | * | 4/1977 | Weckenmann et al. ...... 324/694 |
| 5,682,788 A | * | 11/1997 | Netzer .......................... 324/661 |
| 5,861,758 A | * | 1/1999 | Berberich .................... 324/694 |

* cited by examiner

*Primary Examiner*—N. Le
*Assistant Examiner*—James Kerveros
(74) *Attorney, Agent, or Firm*—Mark M. Friedman (57) ABSTRACT

A capacitive sensor for detecting raindrops on the external surface of a vehicular windshield, relying for its operation on the compensation of the capacitive signals which are due to variation of the dielectric constant of the windshield's glass with temperature, and on the elimination of capacitive signals which result from electrostatic interference or moisture deposition occurring at the inner surface of the windshield. The sensor includes electrodes printed on the internal surface of the windshield and is shielded by a grounded conducting enclosure. Another embodiment of the invention simultaneously senses raindrops on the external side of the window and moister on the internal surface of the windshield.

11 Claims, 9 Drawing Sheets

DIFFERENTIAL WINDSHIELD CAPACITIVE RAIN SENSOR

FIELD AND BACKGROUND OF THE INVENTION

The present invention relates to moisture sensors and, more particularly, to moisture sensors for sensing moisture on an automobile windshield.

The sensor operates on a differential capacitive principle with electrodes deposited on the internal surface of the windshield, which results in higher immunity to undesired influences, and selective response to moisture deposited on either surface of the windshield.

Prior art automotive windshield moisture sensors are invariably based on a single electro-optical concept typically described in U.S. Pat. No. 5,917,603 to Tanaka. In this method, a rain droplet is sensed by measuring the change in the total internal reflection of a light beam off the glass-air interface of the front surface. This method has a limited sensing area, is relatively expensive, and is only suitable for sensing moisture on the outside surface of the windshield.

U.S. Pat. No. 5,923,027 to Stam et al., describes an electro-optical method wherein the brightness of a section of the window image is analyzed to detect rain droplets or fog on the window. A similar approach is disclosed in U.S. Pat. No. 5,020,704 to Buschur.

Attempts have been made to detect rain based on its effect on the resistance, or capacitance, between electrodes deposited on the windshield. Sensors based on these methods are integral with the windshield and are potentially less expensive and less conspicuous.

In U.S. Pat. No. 5,739,430 to Berberich, resistance sensing electrodes are deposited on the external surface of the windshield and are subjected to wear. Extra protection is provided by a sintered glass layer as taught in U.S. Pat. No. 5,783,743 to Weber.

The capacitance sensing method relies on the relatively large dielectric constant of water (approximately 80) as it affects the capacitance between conductive electrodes. The method is described in U.S. Pat. No. 4,805,070 to Koontz et al., U.S. Pat. No. 4,831,493 to Wilson et al., and U.S. Pat. No. 5,668,478 to Buschur.

Typical moisture sensors in which the conductive electrodes are deposited inside the laminate of the "sandwiched" windshield glass are described in U.S. Pat. No. 4,703,237 to Hochstein, in U.S. Pat. No. 4,827,198 to Mueller. in U.S. Pat. No. 4,613,802 to Krause et al., and in U.S. Pat. No. 4,554,493 to Armstrong. In these devices, the capacitive effect of water drops changes the resonant frequency of a resonant circuit.

In prior art capacitive moisture sensors, in which the full thickness of the glass separates the capacitor plates from the water-droplets, the relative change of the capacitance due to water drops is very small, and until recently these devices had difficulty of distinguishing between real signal due to water and false signal due to fluctuations in the window temperature which affects its dielectric constant.

The capacitive rain sensor of U.S. Pat. No. 3,826,979 to Steinmann, uses electrodes deposited on the internal surface of the window in order to sense rain on the external surface of the windshield. In Steinmann's invention, three electrodes are used to shape the fringing electric field in order to increase the signal due to raindrop relative to signal due to the glass. The improvement is marginal since the majority of the measured capacitance is still due to the glass whose temperature dependence still swamps any signal due to rain drops.

In summary, depositing the capacitive plate on the outside surface is not reliable because of the wiper abrasion. deposition in the interlayer is difficult to terminate electrically, and depositing on the inside surface is protected and reliable, but the signal is small. A further disadvantage of prior-art capacitive moisture sensors. regardless of the position of the plates, was their inability to distinguish between moisture on the internal and on the external surfaces of the windshield, making it impossible to automate both the windshield wiper and the defogging means.

For these reasons, capacitive moisture sensors were not in use in the automotive applications. It was not until recently that most of the drawbacks of the capacitive sensors were overcome, as described in U.S. Pat. Nos. 5,801,307 and 5,682,788 and in EP application; EP 0753438, all to Netzer. The improved sensors are stable with temperature, do not obstruct the driver's view, and are "directional", i.e., they can be made selectively sensitive to moisture on either surface of the windshield. Yet, these capacitive sensors have the drawback in that the capacitor plates are embedded within the laminated layer of the front windshield. Such structure imposes limitations on their manufacture and reduce their usage, because not all car windows are laminated. Besides, it is difficult to establish electrical connections to the embedded electrodes.

There is, therefore, a need for a capacitive rain sensor that would overcome the disadvantages of presently known sensors, as described above.

SUMMARY OF THE INVENTION

According to the present invention there is provided an improved automotive raindrop sensor integrally manufactured with the window, with an optional capability to sense moisture on the internal surface of the window. The sensor of the present invention, is inexpensive, does not obstruct the drivers view, is not subject to abrasion, is insensitive to temperature effects on the glass, and is also substantially insensitive to nearby conductive or dielectric objects.

The moisture sensor of this invention is capable of sensing moisture over a large surface area, unlike conventional electro-optical moisture detectors which sample moisture only in a small region, additionally it does not generate false wipe command when touched with a finger.

There is provided a temperature stable capacitive sensor having a sensitive area, for sensing moisture on the external surface of a window having a certain temperature. the sensor comprising: (a) a conductive pattern including at least three capacitive plates disposed on the internal surface of the window, the at least three plates defining at least one sensing capacitor and at least one compensation capacitor; (b) means for generating an output level which changes in response to the moisture and is proportional to the difference between the at least one sensing capacitor and the at least one compensation capacitor; and (c) a shield for protecting at least the pattern from direct moisture condensation and from electrical interference.

There is provided a temperature stable capacitive sensor having a sensitive area for sensing moisture on the internal surface of a window having a certain temperature comprising: (a) a conductive pattern including at least three capacitive plates disposed on the internal surface of the window, the at least three plates defining at least one sensing capacitor and at least one compensation capacitor; (b) means for generating an output level which is indicative of the moisture and is proportional to the difference between the at least one sensing capacitor and at least one compensation capacitor; and (c) a shield for protecting at least the compensation capacitor from direct moisture condensation and from electrical interference.

Other objects of the invention will become apparent upon reading the following description taken in conjunction with the accompanying drawings.

DESCRIPTION OF THE PREFERRED EMBODIMENTS

The present embodiments herein are not intended to be exhaustive and to limit in any way the scope of the invention, rather, they serve as examples for the explanation of the invention and for enabling other skilled in the art to utilize its teaching.

The present invention provides effective means for overcoming the following three main sources of errors that eliminated the use of capacitive rain sensors with electrodes from the inside of the window, according to prior art:
1. Window temperature variations.
2. Moisture condensation on the internal surface of the window.
3. Human body or articles adjacent to the sensor.

The present invention is based on reading the differential current between two capacitors deposited on the windshield. The capacitors are referred to as sensing and compensation capacitors respectively, and are preferably printed and fused into the glass in accordance with prior art technologies of windshield manufacturing.

The advantages of differential moisture capacitive sensors are detailed in U.S. Pat. No. 5,751,071 and in U.S. Pat. No. 5,801,307, both to Netzer, the teachings of which are incorporated here by reference.

In the following description the following terms: plates, electrodes and pattern are interchangeably used.

Figure 1:
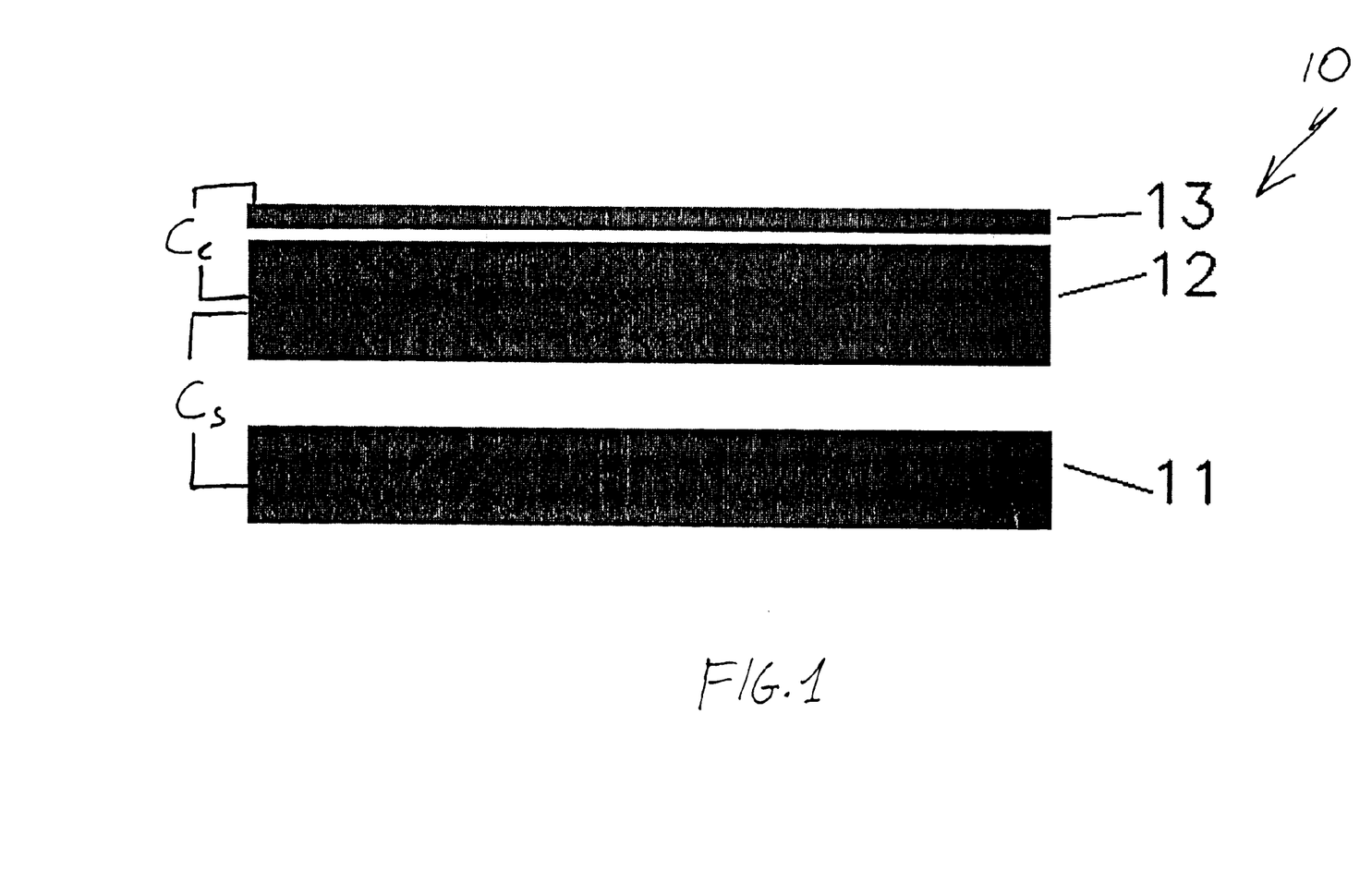
FIG. 1 shows a pattern of the capacitor plate of a sensor according to a first embodiment of the invention.
Figure 2A:
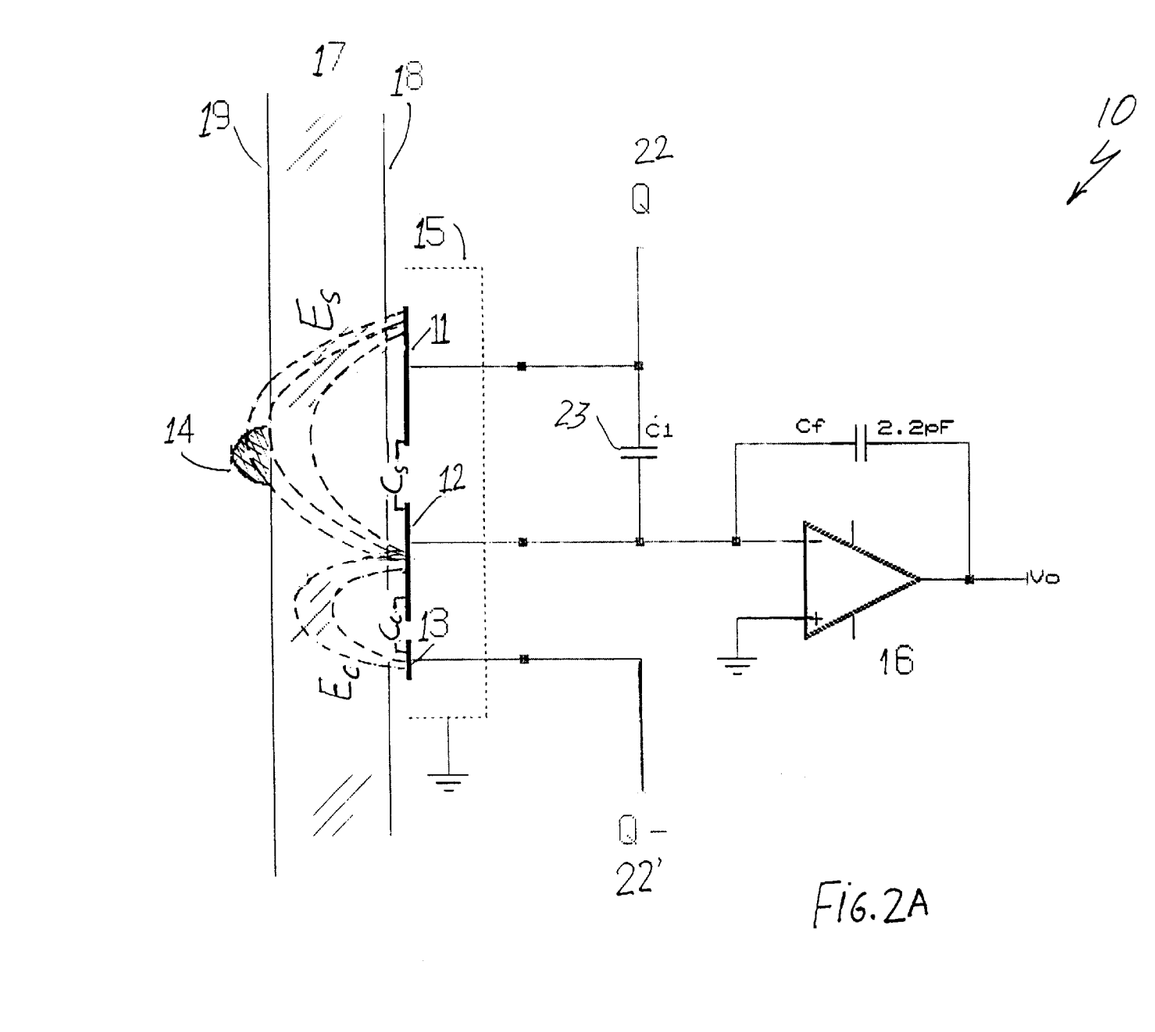
FIG. 2A shows a cross sectional view of the sensor according to the first embodiment of the invention.

FIG. 1 illustrates a typical pattern of the capacitive plates of a rain sensor according to a first embodiment 10 of the invention. FIG. 2A is a schematic sectional view of embodiment 10 in FIG. 1 which includes the input stage of the processing electronics. The electrodes are printed on the internal surface 18 of the window 17, and define two capacitors: namely a sensing capacitor Cs, between the signal plate 12 and the excitation plate 11, and a compensation capacitor Cc between the compensation plate 13 and the signal plate 12.

Excitation plate 11 and compensation plate 13 are excited with two alternating voltages of opposite polarity, 22 and 22', at a typical frequency of 20 kHz. The excitation voltages results in two alternating currents proportional to the respective capacitances and the input current to charge amplifier 16 is indicative of the difference between Cs and Cc which, as will be explained below, is proportional to the moisture on the outside surface 19 of window 17. Charge amplifier 16 converts this differential current into a corresponding alternating voltage Vo.

Figure 2B:
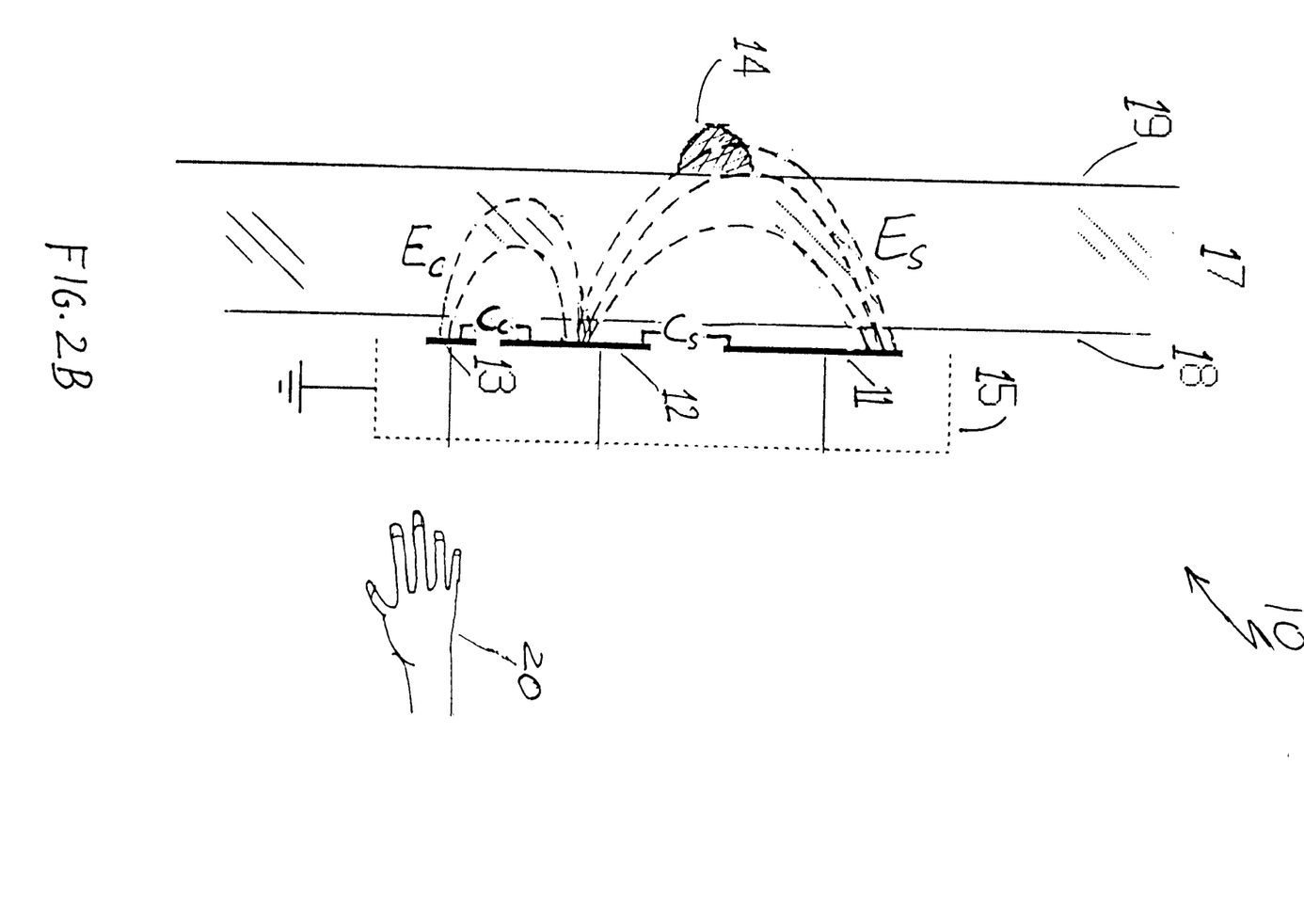
FIG. 2B illustrates the protection of the sensor plates from the influence of nearby objects.

The electrodes 11, 12 and 13 are protected by a grounded electrically conductive shielded 15 against both deposited moisture on the inside surface of the window and capacitive influences due to objects in the vicinity such as a passenger's hand 20, as illustrated in FIG. 2B.

In the embodiment shown in FIG. 2A capacitance Cc is essentially unaffected by raindrop 14 on the external surface 19 of window 17. This is because the fringing electric field Ec between electrode 12 and electrode 13 is confined inside the glass due to the narrow gap and is only marginally affected by the raindrop. On the other hand, the capacitor Cs between signal plate 12 and excitation plate 11, is affected by rain droplet 14 because electric field Es extends beyond the window glass thickness and interacts with rain droplet 14 as long as the droplet is in the sensitive area of the sensor, i.e., between the projected area of plates 11 and 12.

Figure 2C:
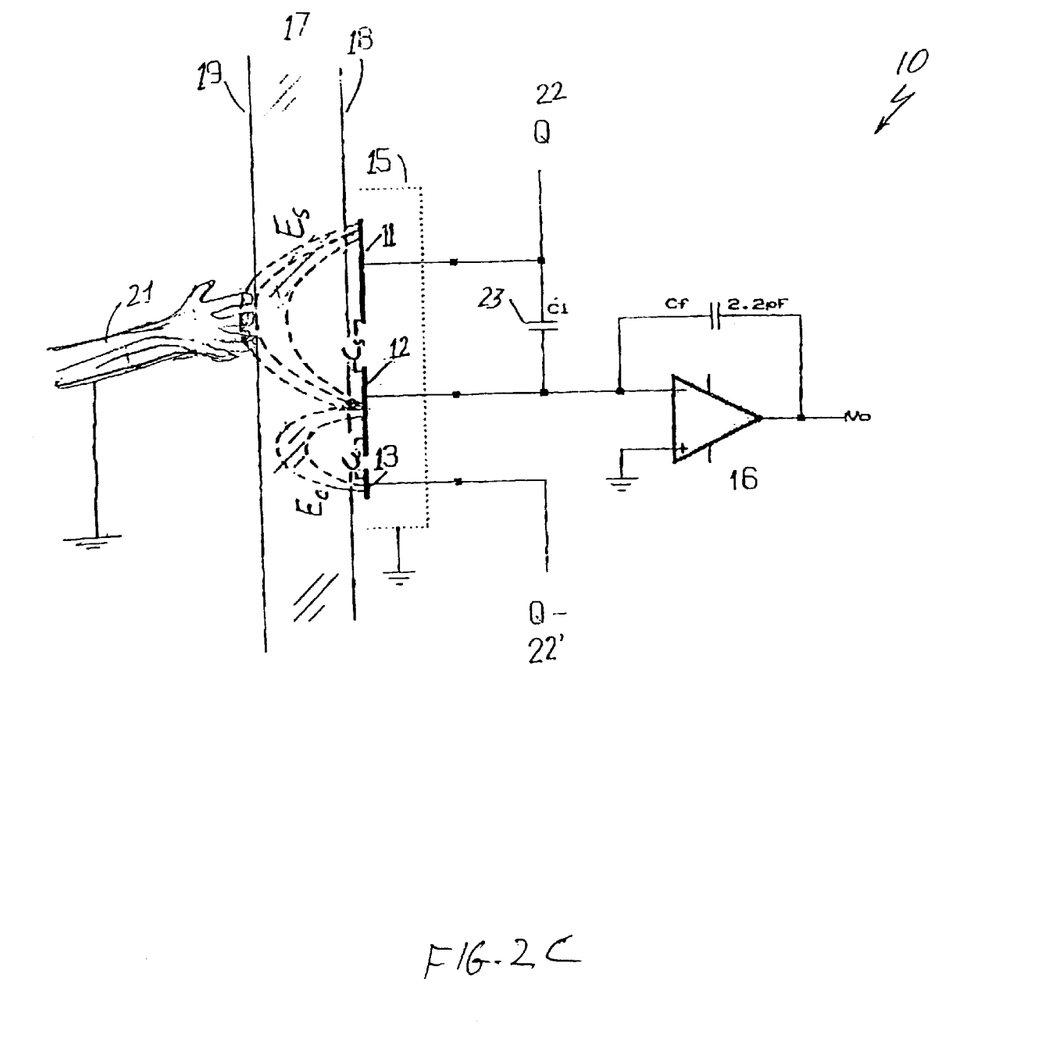
FIG. 2C illustrates the protection of the sensor from false operation due to a touch on the sensitive area.

FIG. 2C illustrates why the present sensor is protected from generating false wipe commands as result of casual touch on its sensitive area, a shortcoming afflicting all electro-optical rain sensors which are currently in use. A person standing on the ground, especially if also touching a standing vehicle, is AC wise practically at ground potential. If his hand 21 touches the sensitive area of the sensor then some of the lines of field Es are shorted to ground and do not reach plate 12. This is equivalent to decreasing the capacitance Cs and will change voltage Vo in an opposite direction to that due to a raindrop, and can thus be discriminated.

Both capacitors Cs and Cc are influenced by changes in temperature which induce variations in the dielectric constant of the window constituents. Subtracting the measured values of the two capacitors may apparently yield a temperature independent indication of the amount of raindrops on the external surface.

However, it was found that the temperature coefficient of compensating capacitor Cc differs from that of sensing capacitor Cs because the dielectric material of each capacitor consists of different proportion of glass, plastic interlayer (in the case of laminated electrodes) and air. Consequently, no full temperature compensation can be achieved by simply subtracting the current passing through Cc from the current which pass through Cs.

In order to achieve substantially full temperature compensation at al relevant temperatures, a discrete capacitor 23 of value $C_1$, preferably with temperature coefficient of zero, is added in parallel to Cs. The value $C_1$ is calculated as follows:

Assuming a linear temperature dependence of the capacitance of Cs and Cc with temperature coefficients $k_s$ and $k_c$ respectively. The parallel combination of Cs and $C_1$ as a function of temperature T is given by:

$$C_s(1+k_sT)+C_1 \tag{1}$$

The compensating capacitor $C_c$ as a function of temperature is given by:

$$C_c(1+k_cT) \quad (2)$$

For zero differential capacitance when the window is dry $C_s$ must equal $C_c$ i.e.:

$$C_s(1k_sT)+C_1=C_c(1k_cT) \quad (3)$$

To satisfy the temperature dependent part of equation 3 it is needed that:

$$C_s=C_c(k_c/k_s) \quad (4)$$

To satisfy equation 3 with regard to the temperature independent terms it is needed that:

$$C_1=C_c-C_s \quad (5)$$

To design a sensor pattern $k_s$ and $k_c$ should he determined and the pattern is set to satisfy equations 4 and 5. It should be emphasized that capacitor $C_1$ does not have to be temperature independent, as long as its temperature dependence is taken into account.

Since the sensor comprises opaque electrodes and shield box it may obscure the vision of either the driver or the front passenger. To minimize obstruction as much as possible it is preferably located on the lower edge of the windshield. When the window includes a black ceramic frame coated around its periphery, the sensor is preferably placed on top of it—since the black ceramics is non conductive and does not interfere with the sensing.

Figure 3A:
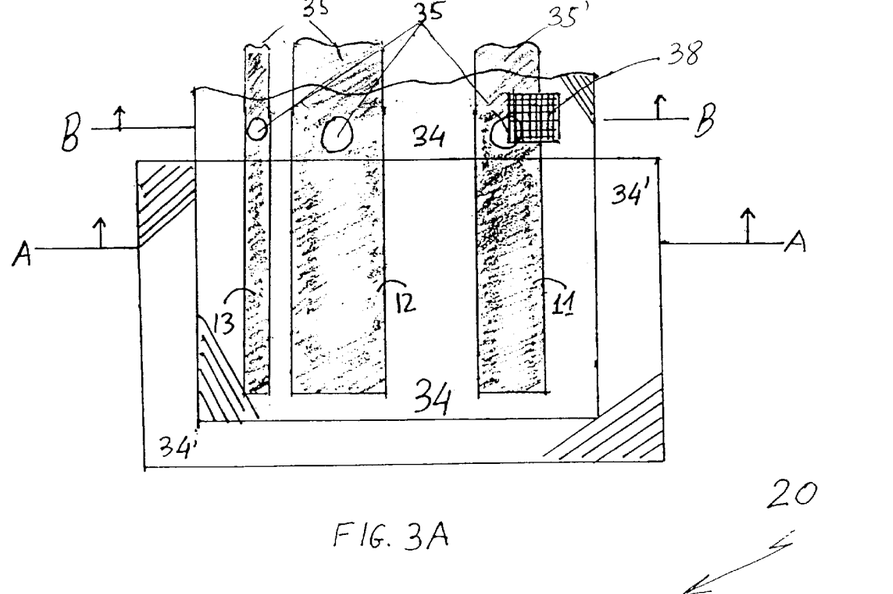
FIGS. 3A, 3B and 3C show the top view and two cross sectional views of the sensor according to a second embodiment of the invention.
Figure 3B:
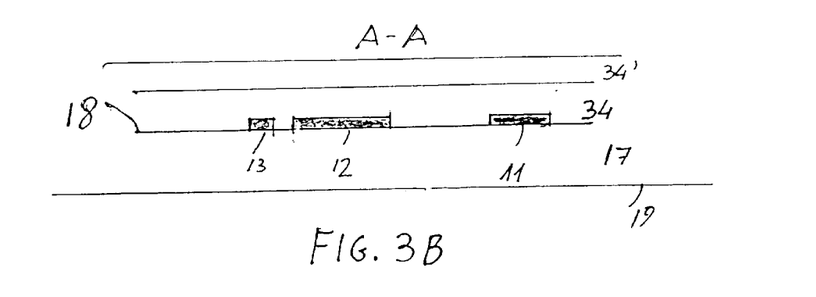
Figure 3C:
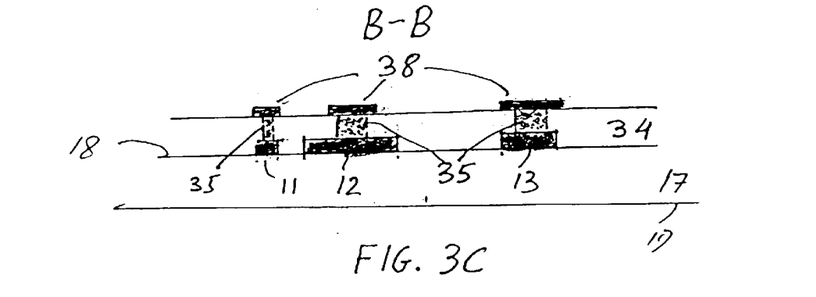

Another method of shielding the sensor electrodes is illustrated by embodiment 20, shown in FIGS. 3A, 3B and 3C. Plates 11, 12, and 13 are selectively coated with an electrically insulating layer 34 e.g. of the same ceramic used for the peripheral window frame, leaving some electrode exposed areas 35' for interconnecting through areas 3S'. A conductive layer 34' is then applied on top of layer 34, which is grounded to serve as a shield. The rest exposed area 35' of electrodes 11, 12 and 13 is protected by a small conductive enclosure 15 shown in FIG. 4 which, preferably, also protects the processing electronics board 36. Optional conductive pads 38 that touches the electrodes 11, 12 and 13 through access holes 35 in layer 34, provide extra area for interconnection. This shielding method has the advantage that the sensing area can be as large as desired, substantially without increasing the dimensions of enclosure 15.

Implementation of the conductive pattern on the windshield can be made in different ways, such as hot stamping—which is a transfer method known in the art. Preferably, the conductive pattern is made by screen printing a silver based thick film which is then fused into the glass. This material is commonly used for the heater grid in the rear window and is known to develop, over time, a high resistance oxide film.

Figure 4:
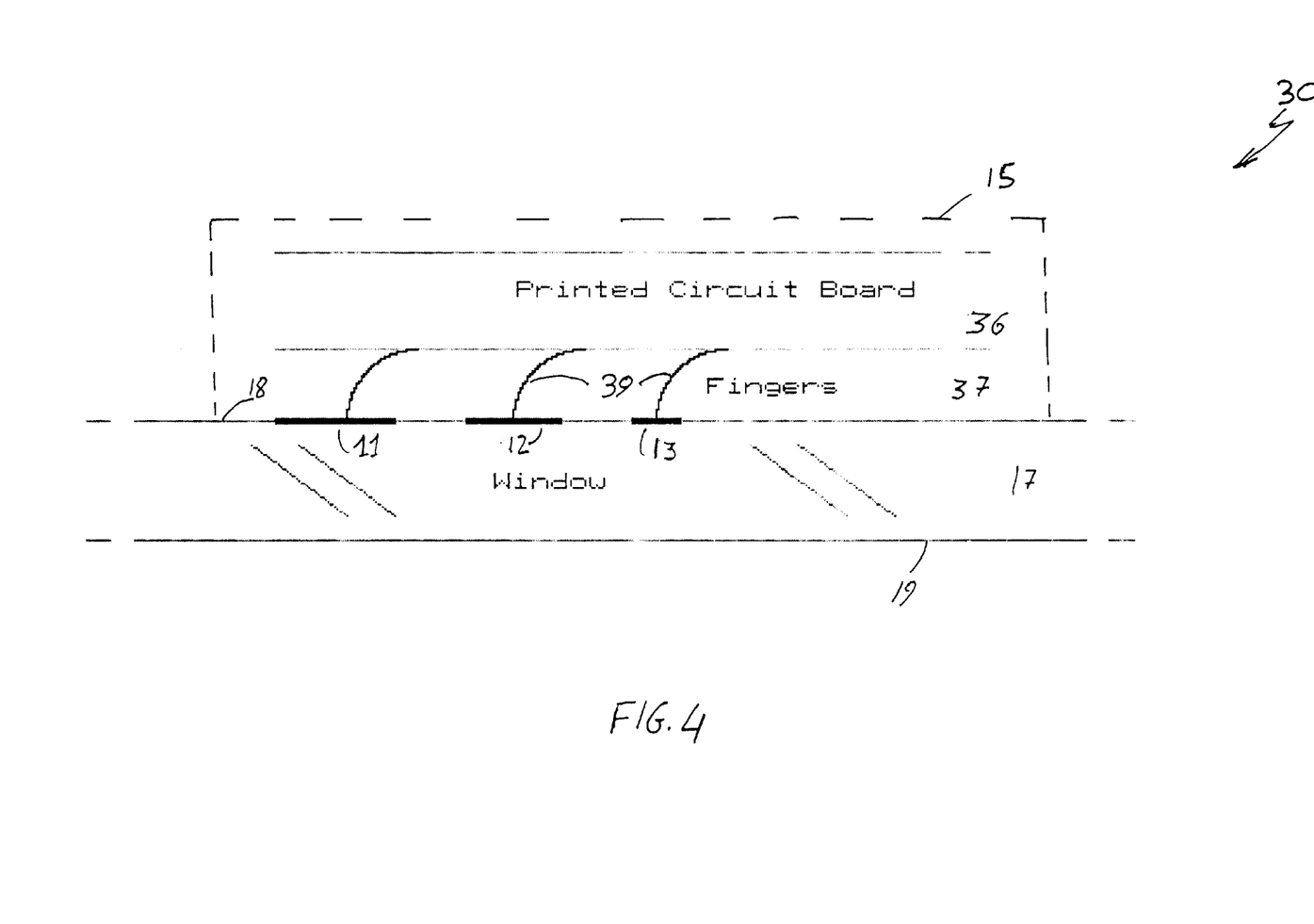
FIG. 4 is a cross sectional view of the third embodiment of the invention.

FIG. 4 also illustrates a preferred method of electrically connecting the circuit board 36 with the electrodes 11, 12 and 13 (or with the pads 38 that touch the electrodes through access holes 35), that overcomes the contact resistance. In this method flexible conductive fingers 39 with sharp tips are soldered to the bottom side of the board 36 in the spacing 37, the increased contact pressure in the tip area results in localized cold welding that guarantees a reliable connection.

Figure 5:
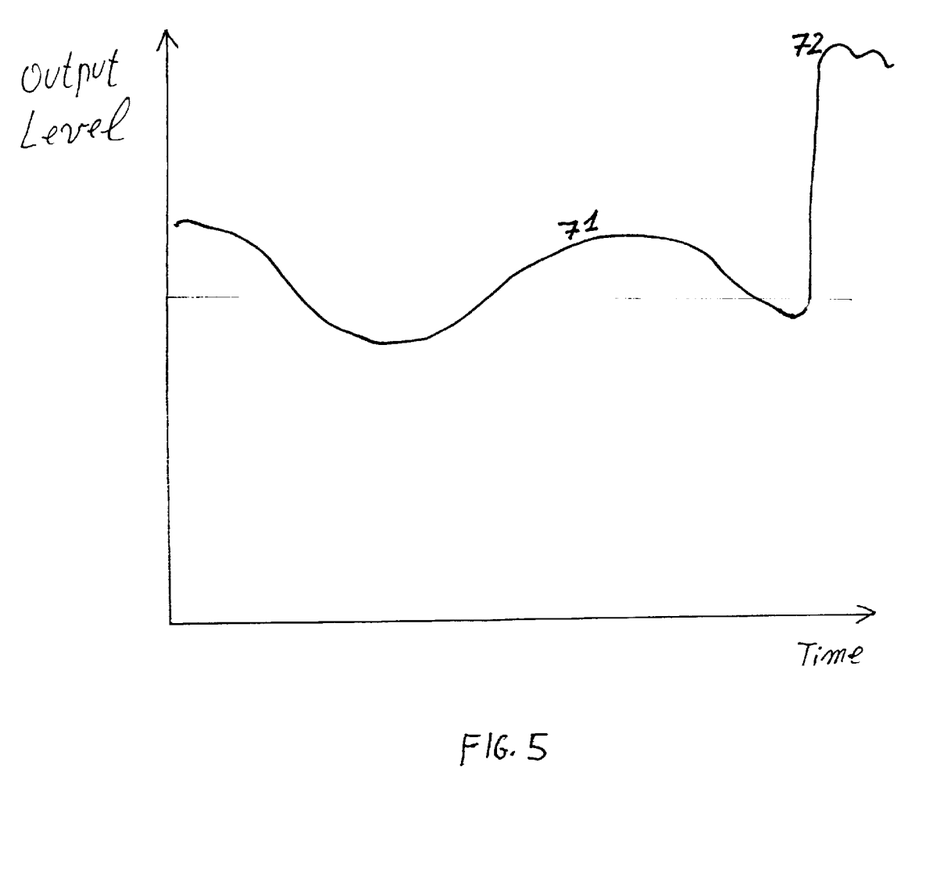
FIG. 5 shows an exaggerated plot of the sensor output versus time.

The temperature compensation of the rain sensor as described above is satisfactory in most situations, however, in applications where the detection of very small droplet, as in drizzle, the signal level may be extremely small as to be undetectable in the presence of unstable baseline of the output voltage. A wiper command is initiated by comparing the signal level to a threshold level and an unstable baseline may generate false wipe command. FIG. 5 illustrates an unstable baseline that may result because of incomplete temperature compensation due to the signal and compensation plates sensing glass of different temperatures. This situation may occur as a result of differences between the temperature outside and the temperature inside the vehicle. To overcome such effect use is made of the following two observations:

1. The rate of change of the baseline versus time due to temperature variations is much lower than that due to raindrops.
2. The change due to temperature may be in either direction, whereas that due to raindrop is always in one direction—positive for the sake of the discussion.

In the preferred embodiment of the invention the baseline 71 of the output voltage is periodically sampled and each sample is compared with the previously stored one. If the deviation is negative it is assumed that it is due to temperature and the threshold is updated by subtracting this deviation. If the deviation is positive but smaller than a predetermined value (preferably smaller than the signal due to the smallest droplet), it is assumed that the difference is due to temperature variation and the threshold is updated, as before. If the sensed deviation 72 relative to the threshold is positive and larger than the predetermined value, the threshold is not updated and a wiper command is initiated.

Figure 6:
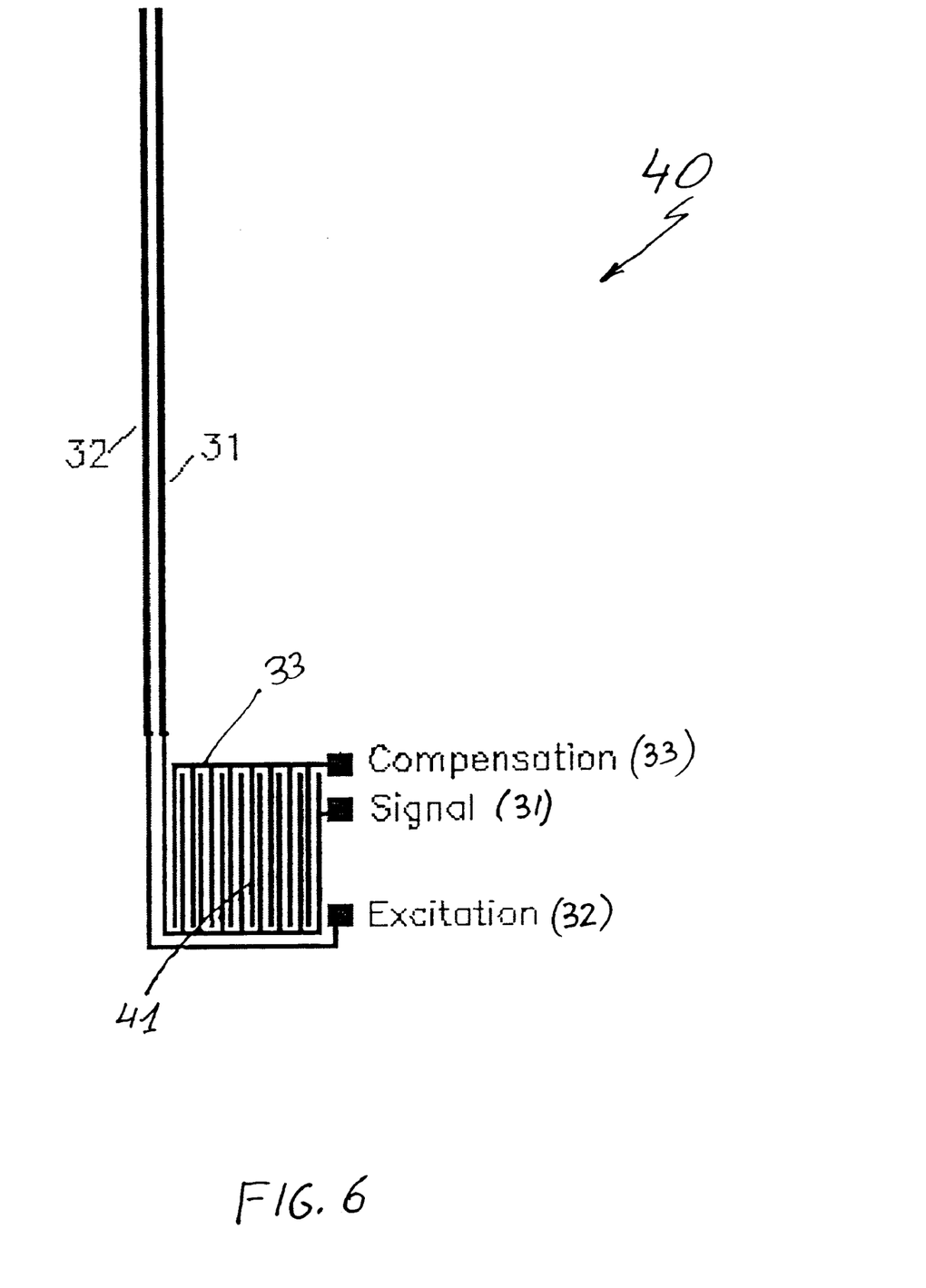
FIG. 6 shows a pattern of printed capacitor plates for an improved prior art sensor for sensing moisture on the internal surface of a window.

FIG. 6 shows an embodiment 40 of the invention which is an improvement over the capacitive moisture sensor described in U.S. Pat. No. 5,751,071 to Netzer. As opposed to the previously described embodiments, this sensor is for sensing moisture condensed on the patterned side of a surface in general, and oil the inner surface of the window in particular. by measuring capacitance changes between two elongated plates 31 and 32 which are also printed on the inner surface of the window, but unlike the rain sensing plates, are exposed to deposited moisture.

As long as the condensed moisture is not frozen, the added capacitance is easily detected, however, it was found that when the condensed moisture is frozen, it's effect on the measured capacitance between the electrode 31 and 32 is reduced. This is because the dielectric constant of water, which is about 80 at temperatures, which are above zero degrees Centigrade, diminishes as the temperature drops and becomes comparable to that of glass, which is about 5 at low enough temperatures.

The glass contribution to the measured capacitance can therefore no longer be neglected, and since the dielectric constant of the glass itself drops with temperature, the total measured capacitance decreases further as temperature drops down. The net result is an inadequacy of the original method, as described in the above cited patent at subzero temperatures.

The pattern 41, shown in FIG. 6 compensates for changes in capacitance measured between signal electrodes 31 and 32 due to temperature variations of the window's glass. Pattern 41 constitutes capacitance 33 that, similarly to that of the compensating capacitance Cc in embodiment 10, enables a differential compensation of temperature effects. This pattern is kept dry e.g. by means of a metal or a thick film shield, as described above in regards to the rain sensor. The differential operation of the improved sensor in embodiment 40 enables reliable detection of frost on the inner surface of a window down to −40° C. and below.

Since the operation of this moisture sensor is similar in principle to that of the rain sensor in embodiment 10 shown in FIG. 2, its processing electronics may be similar. However, the intimacy of the sensor plates and the moisture results in a higher signal level and compensation of the glass thermal effect is less critical the discrete capacitor 23 used in embodiment 10 is therefore not mandatory.

Figure 7:
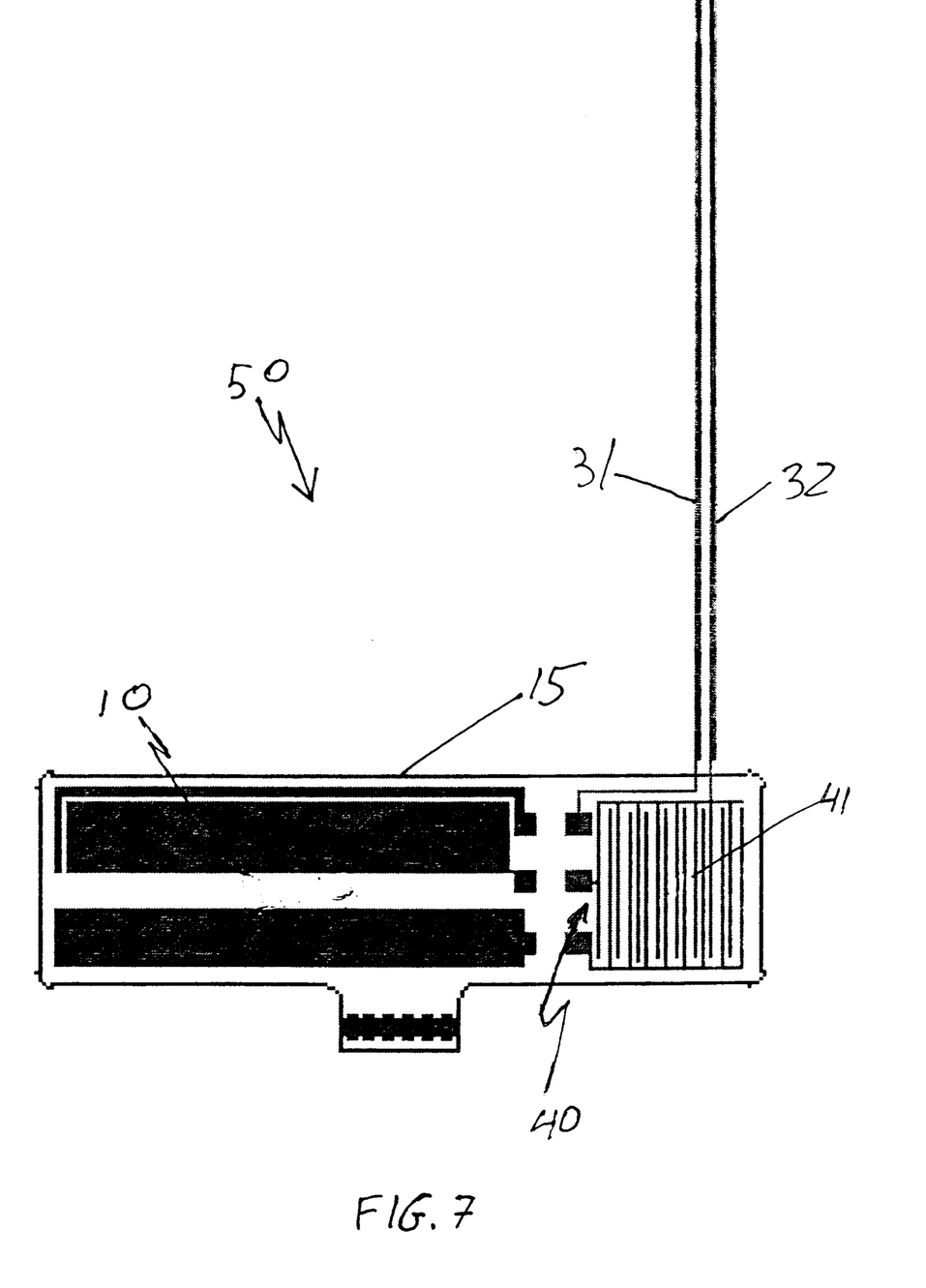
FIG. 7 shows a pattern of printed capacitor plates for a dual purpose sensor for sensing moisture on both surfaces of a window.

FIG. 7 illustrates still another embodiment 50 of the present invention. It shows a top view of a printed conductive pattern for a combined rain and moisture sensor. Embodiment 50 incorporates embodiment 10 and embodiment 40 in one dual sensor that is sensitive to the rain on the external surface, with rain sensor electrodes 10 and to moisture on the inner surface of the windshield, with sensor plates 31 and 32.

These plates can shaped differently, or extend any length, for example, they may encircle partly, or wholly, the periphery of the window. The pattern 10 is enclosed by a grounded shield 15, preferably common to pattern 41 and to the processing electronics circuit board.

While the invention has been described with respect to a limited number of embodiments, it will be appreciated that many variations, modifications and other applications of the invention may be made, such as application to trains and airplanes windows for sensing moisture on external vehicular mirrors and for other applications.

What is claimed is:

1. A window provided with a temperature stable capacitive sensor deployed on an internal surface for sensing moisture on an external surface, the window comprising:

(a) a window having an internal surface and an external surface;

(b) a conductive pattern including at least three capacitive electrodes disposed on said internal surface, said at least three capacitive electrodes including at least a first pair of electrodes defining a sensing capacitor and at least a second pair of electrodes defining a compensation capacitor, wherein a spacing between said second pair of electrodes is smaller than a spacing between said first pair of electrodes such that said sensing capacitor is sensitive to moisture on said external surface of said window and such that said compensation capacitor is substantially insensitive to moisture on said external surface of said window;

(c) a shield for electrically shielding at least part of said conductive pattern; and (d) circuitry associated with said at least three capacitive electrodes and configured to generate an output which varies as a function of a difference in capacitance between said sensing capacitor and said compensation capacitor.

2. The window of claim 1, wherein said circuitry includes a discrete capacitor connected in parallel to said compensation capacitor.

3. The window of claim 1, wherein said shield is implemented at least in part as a housing, said circuitry being deployed within said housing.

4. The window of claim 1, wherein said circuitry includes decision means with a threshold value to provide a rain indication.

5. The window of claim 4, wherein said decision means is configured to generate said rain indication only when a rate of change of said output exceeds a predetermined rate value.

6. The window of claim 1, wherein said at least three capacitive electrodes are fused into said window.

7. The window of claim 1, wherein at least a portion of said shield includes: a first layer of an electrically insulating material deposited on at least part of the area between said at least three capacitive electrodes; and a second layer of an electrically conductive material deposited on said first layer.

8. The window of claim 1, further comprising a second conductive pattern including a second set of electrodes applied to said internal surface of said window and additional circuitry associated with said second conductive pattern and configured to identify the presence of condensation on said internal surface of said window.

9. The window of claim 8, wherein electrical connections to said electrodes are implemented via cold welds.

10. The window of claim 1, wherein electrical connections to said electrodes are implemented via cold welds.

11. The window of claim 1, wherein said window includes a ceramic opaque frame coated around a periphery of said window and wherein said sensor is at least partially disposed in the area of said ceramic opaque frame.

* * * * *